United States Patent
Manin

(10) Patent No.: US 11,567,343 B2
(45) Date of Patent: Jan. 31, 2023

(54) EAR ADAPTER APPARATUS FOR DISTRIBUTING FORCE AGAINST AN EAR

(71) Applicant: Eugene Manin, Kalamazoo, MI (US)

(72) Inventor: Eugene Manin, Kalamazoo, MI (US)

(*) Notice: Subject to any disclaimer, the term of this patent is extended or adjusted under 35 U.S.C. 154(b) by 450 days.

(21) Appl. No.: 16/713,151

(22) Filed: Dec. 13, 2019

(65) Prior Publication Data

US 2021/0181535 A1  Jun. 17, 2021

(51) Int. Cl.
*G02C 5/14* (2006.01)
*G02C 11/00* (2006.01)
*A42B 3/16* (2006.01)
*A61F 11/14* (2006.01)

(52) U.S. Cl.
CPC ............ *G02C 5/143* (2013.01); *A42B 3/16* (2013.01); *G02C 11/10* (2013.01); *A61F 11/14* (2013.01)

(58) Field of Classification Search
CPC ...... G02C 5/143; A42B 3/16; A41D 2400/36; A41D 2400/38; A61F 11/06; A61F 11/10; A61F 11/12; A61F 11/14
USPC .............................................. 2/423; 351/122
See application file for complete search history.

(56) References Cited

U.S. PATENT DOCUMENTS

| | | | | |
|---|---|---|---|---|
| 4,863,257 | A * | 9/1989 | Morgan | G02C 5/143 351/123 |
| 5,042,933 | A * | 8/1991 | Lear | G02C 5/20 351/111 |
| 8,733,926 | B2 * | 5/2014 | Stewart | G02C 5/143 351/122 |
| 2014/0231474 | A1 * | 8/2014 | Sugihara | A45F 5/00 224/181 |
| 2015/0246510 | A1 * | 9/2015 | Yoshinaga | B32B 7/12 428/213 |
| 2015/0293374 | A1 * | 10/2015 | Wanderer | G02C 5/143 351/123 |
| 2018/0292674 | A1 * | 10/2018 | Bond | A61F 9/029 |

* cited by examiner

*Primary Examiner* — Darryl J Collins
(74) *Attorney, Agent, or Firm* — McGarry Bair PC

(57) ABSTRACT

An apparatus for distributing a force to a user's ear resultant of a user's earwear. A cushion can be adapted to fit between a user's ear and a user's head. A curved channel defining a guide channel can pass alone the cushion. A line can extend through the cushion and the curved channel for attaching the ear adapter assembly to a user's eyewear. The cushion can distribute a force applied to a user's ear from a user's earwear to minimize deformation of the user's ear resultant of the compressive force from the user's earwear.

19 Claims, 11 Drawing Sheets

EAR ADAPTER APPARATUS FOR DISTRIBUTING FORCE AGAINST AN EAR

BACKGROUND OF THE INVENTION

"Eyewear" can be any object worn over one or both eyes of a user. One example can include glasses having an eyewear temple that, for instance, rests upon or is supported by the pinna portion of a user's ear. In another aspect, "earwear" can be any object, device, or covering worn by the user that at least partially covers or extends over a portion of a user's ear. Examples of earwear can include headphones, headsets, helmets, headgear, or earmuffs. Earwear can utilize a compressive force, relative to the user's ear or head, to remain in place during use. Often, during concurrent wearing of eyewear and earwear, the compressive force of the earwear compresses a portion of a user's ear against the eyewear, and as such, causing a pinch point with the eyewear, for example, which can cause discomfort for the user.

BRIEF DESCRIPTION OF THE INVENTION

In one aspect, the disclosure relates to an ear adapter assembly including a curved channel forming a guide channel. A cushion at least partially surrounds the curved channel and is adapted to fit between a portion of a user's ear and a side of a user's head. A line extends along the guide channel of the curved channel and through at least a portion of the cushion.

In another aspect, the disclosure relates to an ear adapter assembly for eyewear including a cushion having a front end and a bottom end, and adapted to be positioned between a user's ear and a user's head. A curved channel having a hollow body extends at least partially through the cushion and a portion extending from the front end of the cushion. A line extends through the cushion and the curved channel and forms a loop extending from the front end of the cushion. An eyewear loop secured by the loop is adapted to connect to a temple of the eyewear. Tensioning of the line secures the eyewear loop to the temple of the eyewear or shapes the cushion in an area between the user's ear and the user's head.

In another aspect, the disclosure relates to an ear adapter assembly including a curved channel having a hollow body. A cushion connects with the curved channel and is adapted to fit between a pinna portion of a user's ear and a side of a user's head. A line extends axially along the hollow body of the curved channel and through at least a portion of the cushion. The cushion is contoured such that an applied lateral force relative to the pinna portion is distributed by the cushion to reduce deformation of the pinna portion.

DETAILED DESCRIPTION OF THE INVENTION

Aspects of the disclosure described herein are directed to a method and apparatus for distributing a compressive force applied to a pinna portion of a user's ear from earwear. Aspects of the disclosure can further pertain to an assembly and method for relieving painful ear deformation resultant from concurrent wearing of eyewear and earwear. Specifically, when the compressive force applied from earwear is in a direction toward a user's head, the pinna portion of a user's ear is compressed, forced, pressured, or otherwise biased toward the head, in the compressive force direction. Specifically, the painful ear deformation is caused by the compressive force of the earwear against the pinna portion of the ear about a temple portion of the eyewear. In instances where the user is wearing eyewear or where an eyeglasses frame or eyewear temple portion is worn wrapping around the ear back, the compressive force from the earwear can bend, depress, or otherwise deform a portion of the user's ear relative to the head or eyewear. This deformation of the pinna portion of the user's ear relative to the head or eyewear can be experienced by the user in the form of discomfort, pain, or the like, either immediately or over a period of time.

As used herein, the term "set" or a "set of elements" can be any number of respective elements, including only one. All directional references (e.g., radial, axial, upper, lower, upward, downward, left, right, lateral, front, back, top, bottom, above, below, vertical, horizontal, clockwise, counterclockwise) are only used for identification purposes to aid the reader's understanding of the disclosure, and do not create limitations, particularly as to the position, orientation, or use thereof. Connection references (e.g., attached, coupled, connected, and joined) are to be construed broadly and can include intermediate members between a collection of elements and relative movement between elements unless otherwise indicated. As such, connection references do not necessarily infer that two elements are directly connected and in fixed relation to each other.

Figure 1:
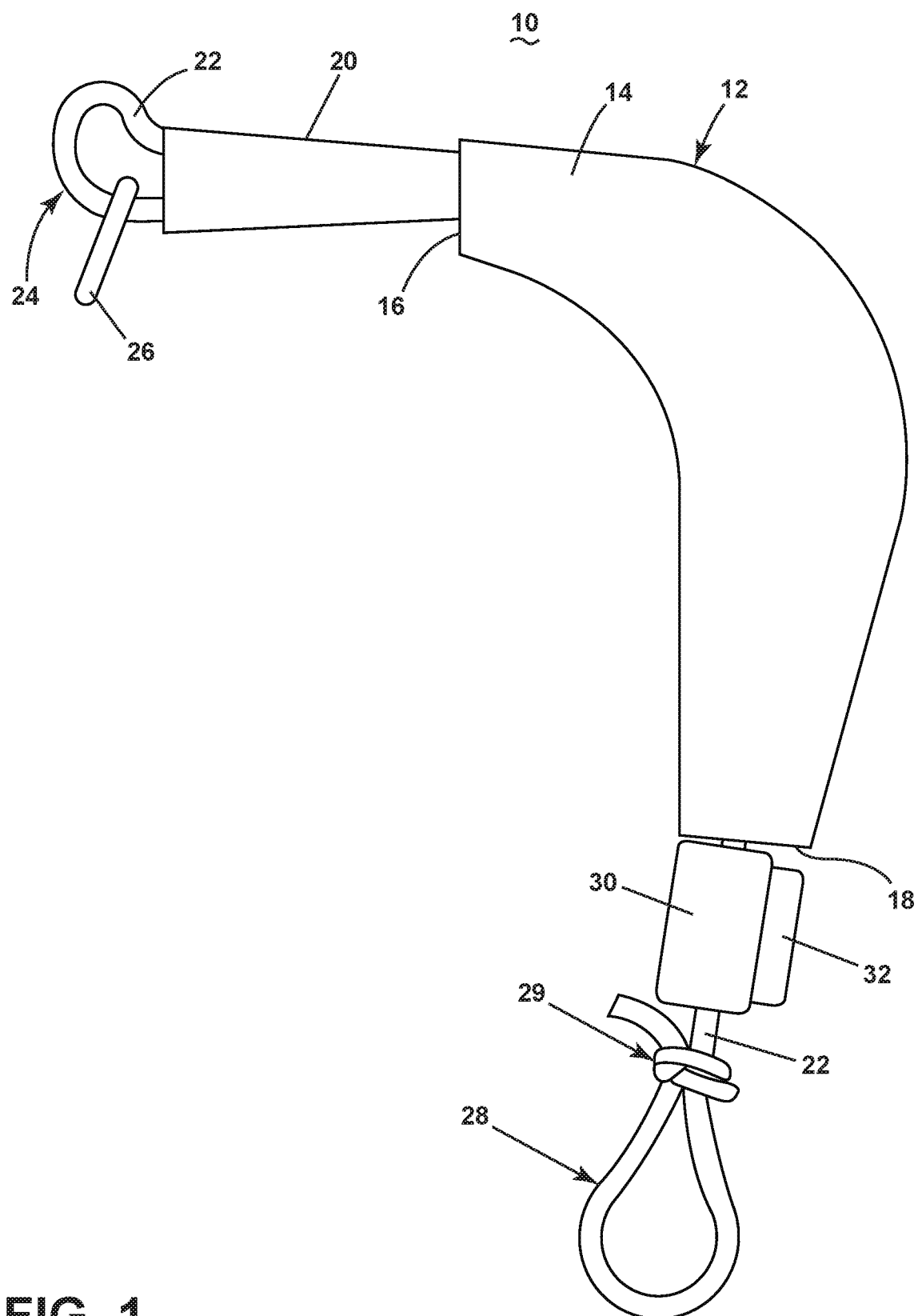
FIG. 1 is a side view of an ear adapter assembly including a cushion.

Referring to FIG. 1, an ear adapter assembly 10 can include a support or a cushion 12 having a body 14 with a first end as a front end 16, and a second end as a bottom end 18. In one non-limiting example, the cushion 12 can include, comprise, or be made of a deformable material, such as foam or memory foam. The material need not be uniform, just able to resist compression. Additionally, it is contemplated that the cushion 12 is made of multiple materials, or multiple layers of materials best described in FIG. 9, or any suitable material providing localized support against ear deformation, as may be desirable for comfort. Furthermore, it is contemplated that the cushion 12 need not be deformable, but can be made of a support material, such as polystyrene, for example, configured to resist or prevent deformation. A funnel-shaped securing element 20 is positioned at the front end 16 of the cushion 12. The securing element 20 can have an increasing width or cross-sectional area, relative to the portion of the securing element 20 proximate to the front end 16, as shown. In another non-limiting aspect, it is contemplated that the cross-sectional area of the securing element 20 can remain constant, and need not be shaped as a 'funnel.' It should be appreciated that the 'funnel' shaped securing element 20 serves as a stop for terminal ends of lines extending through the securing element. Regarding securing elements 20 that are not shaped as a funnel, such elements should be shaped or implemented to provide for stopping or securing a terminal end of a line through the securing element. In non-limiting examples, the securing element 20 can be alternatively be an adhesive, such as tape, glue, or a crimp, or can be any other suitable fastener, and need not be a securing element 20 or have an expanding cross-sectional area. Ideally, the securing element 20 or other suitable fastener is configured to minimize size and bulk, decreasing overall weight of the ear adapter assembly 10 as well as bulk around the user's ear during use.

An elongated tension element shown as a cable or a line 22 extends through the cushion 12 and the securing element 20. Non-limiting examples of the line 22 can include a cable, string, or rope, an elastic band, bungee, chain, cord, or any suitable similar structure having a length, which can be pulled or is tensionable in the direction of the length. The line 22 can alternately consist of either a more-elastic material or a combination of less-elastic material and a tensioning element, such as, but not limited to, a spring. Thus, the line 22 can include fixed length structures (e.g. a non-stretchable material) or variable length structures (e.g. an elastic band or other stretchable material). A loop 24, or other suitable eyewear fastener or terminal adapted to connect to an eyewear temple, can be formed by the line 22 extending from the securing element 20 and returning into the interior of the securing element 20 to attach or affix to the interior of the securing element 20. The securing element 20, in turn, secures, fixes, or fastens the line 22 by way of at least one of the ends of the line 22 forming the loop 24. In another example, the line 22 need not fasten within the securing element 20, but can be free-hanging, such that the loop 24 can be formed when desirable by fastening the line 22 by the securing element 20. A connector shown as an eyewear ring 26 can also be provided at the loop 24, and secured on the loop 24, as shown. In one non-limiting example, the eyewear ring 26 can also be a loop, a ring, a rubber band, an o-ring, or any other flexible closed or closable loop, and can be made of rubber, plastic, twine, or metal, although additional geometric and material configurations or compositions are envisioned. In another example, the eyewear ring 26 need not be wholly circular, but can be any suitable shape, such as an oval in one example. Such a flexible type of eyewear ring 26 can provide for deforming and partially inserting into the securing element 20 during tensioning of the line 22. A rubber eyewear ring 26 could also provide a frictional grip once pulled into the securing element 20. In another non-limiting example, the eyewear ring 26 can have a break in the loop, such as a hook and gate configuration, not unlike a carabiner, or other similar clasping mechanism. In another non-limiting example, the eyewear ring 26 can be contoured, shaped, sized, or the like such that the eyewear ring 26 cannot pass through, about, or around the securing element 20. While shown herein as a single line 22, it should be appreciated that there may be multiple lines incorporated with the ear adapter assembly 10. For example, a first line may be used to connect the eyewear ring 26 to the temple of eyewear, while a second line is used to modulate the shape of the cushion.

Opposite of the front end 16, proximate to the bottom end 18 of the cushion 12, the line 22 can terminate at an adjustment loop 28, shown as formed by an exemplary fastener shown as a knot 29. Alternatively, the fastener could be a crimp, adhesive, or other similar fastener to form the adjustment loop 28 or attach another terminal end element. However, additional terminal ends are envisioned instead of the adjustment loop 28, such as a knot, tab, bead, chin-strap for a helmet, carabiner, hook, fastener, or any other suitable element to facilitate handling by the user either to draw and tighten the line 22 or to secure the ear adapter assembly 10. The adjustment loop 28 can be suitable for hanging or storing the ear adapter assembly 10 when not in use. Additionally, other means of forming the adjustment loop 28 are contemplated, such as a metal clasp, tie, or other suitable fastener to secure an end of the line 22 to itself to form the adjustment loop 28, as opposed to the knot 29. Furthermore, any suitable element to serve as a restraint to prevent the line 22 from receding into the cushion 12 and as a grab point for a user to tension the line 22 is contemplated. Such a grab point can include an attached decorative item, such as a knob, bead, figurine, pendant, jewelry, charm or otherwise, in non-limiting examples.

A clasp 30 can be provided on the line 22 between the knot 29 and the bottom end 18 of the cushion 12. The clasp 30 can include an actuator, such as a button 32, for selectively clasping or unclasping, or fixing or unfixing the clasp 30 relative to the line 22. In this sense, the clasp 30 can be movably slid along the line 22 when unclasped or unfixed, and then re-clasped or re-fixed at a new longitudinal position relative to the line 22. In one non-limiting example, the clasp 30 can be biased toward the clasped or fixed configuration, such that in the absence of intervention, it will remain longitudinally fixed relative to the line 22. In one non-limiting example, the clasp 30 can be integrated with the bottom end 18 of the cushion 12.

Figure 2:
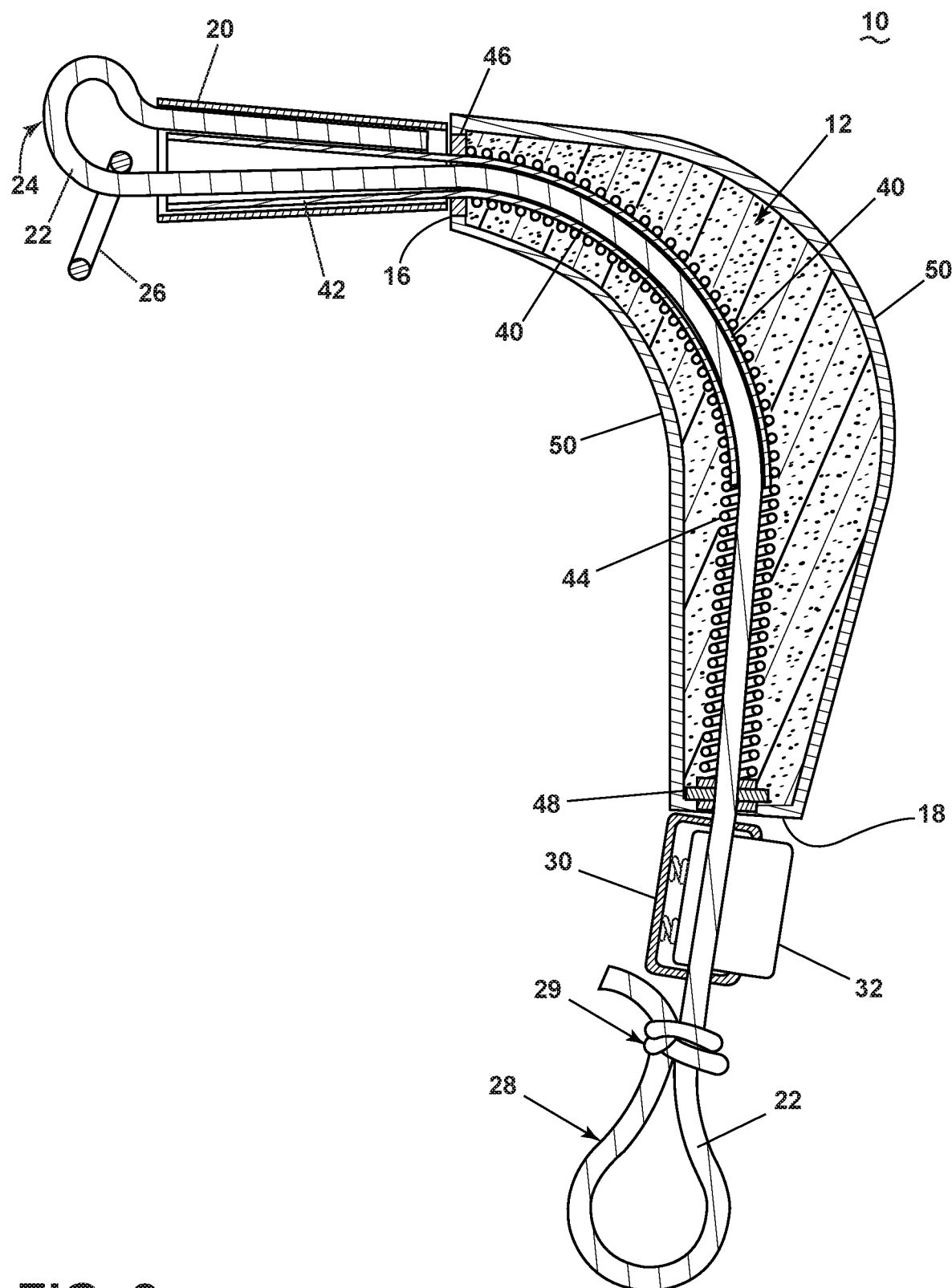
FIG. 2 is a cross-sectional view of the ear adapter assembly of FIG. 1.

Referring now to FIG. 2, the cross-sectional view of the ear adapter assembly 10 illustrates a first guide member, shown as a curved channel 40, extending through at least a portion of the interior of the cushion 12, and a second guide member, shown as a second flared channel 42, extending through at least a portion of the interior of the securing element 20. As illustrated and described herein, the securing element 20 provides a securing surface for the line 22 exterior of the flared channel 42 portion of the curved channel 40 to form the loop 24. Alternatively, it is contemplated that the line 22 may be secured interior of the flared channel 42. In such an example, the ear adapter assembly 10 may be used without securing element 20. The loop 24, optionally, prevents the line 22 from receding into the securing element 20 and keeps the line from dangling when attached to a mount structure, such as eyewear. Similarly, the securing element 20 prevents the cushion 12 from extending into a forward position such that the securing element 20 becomes internal of the cushion 12. It should be appreciated that the securing element 20 need not be a funnel-shape complementary to the flared channel 42, but rather can be any suitable fastener to secure the line 22 to the exterior of the flared channel 42. Similarly, the flared channel 42 need not be flared, but can be any suitable shape serving to secure the line 22 against the flared channel 42 or to prevent the loop and channel 42 from receding into the cushion 12. While the illustrated example shows the curved channel 40 only partially extending through the cushion 12, the curved channel 40 can extend fully through the cushion 12, or need not be separate from the cushion 12 such as integral with the cushion 12. The curved channel 40 can have a hollow body, such as a tube or conduit permitting passage and tensioning of the line 22 within the curved channel 40. Alternatively, the curved channel 40 can be any suitable guiding element, which allows for movement and tensioning of the line 22 within or relative to the cushion 12, and need not be curved or wholly curved, but can be linear, partially curved, or a combination thereof. Non-limiting examples for the curved channel 40 can include guide rails, support beam, through opening, a spiraling tunnel, or the like. In another non-limiting aspect of the disclosure, curved channel 40 can include a rigid or semi-rigid flexible component or construction, to maintain the shape or form of the cushion 12 around or about the curved channel 40. In this sense, an aspect of the curved channel 40 can provide at least a portion of the contouring, shaping, or other geometric configuration for the cushion 12. Stated another way, the curved channel 40 can form a 'backbone' or 'spine' for the ear adapter assembly 10. Alternatively, it is contemplated that the curved channel 40 or a portion thereof can be flexible to permit flexion and formation of the cushion 12. Specifically, in an example where the curved channel 40 extends fully through the cushion 12, a flexible curved channel 40 would be advantageous in adapting the shape of the cushion 12 through tensioning of the line 22, such as at the bottom of the cushion 12 to conform to the shape of the pinna portion of an ear. It should be appreciated, however, that a flexible curved channel 40 need not extend fully through the cushion 12.

The flared channel 42 can include a diverging portion forming the flared channel 42, having an increasing cross-sectional area exterior of and extending away from the cushion 12. The flared channel 42 can be complementary to the shape of the securing element 20 described herein, or the securing element being complementary to the flared channel 42. In one alternative example, the flared channel 42 need not be flared, but can be an extension of the curved channel 40 having a similar shape or diameter. In yet another example, the ear adapter assembly 10 can be formed without either of the securing element 20 or the flared channel 42, and a suitable fastener, such as a crimp, can be used to secure the end of the line 22 to itself or any other suitable element, portion, or aspect of the ear adapter assembly 10 to form the loop 24.

A spring 44 can be provided within the cushion 12, such as surrounding or integral with the curved channel 40. The spring 44 can alternatively be any elastic line or compressive elements similar to that of a spring. A first bushing shown as a front bushing 46 is provided at the front end 16 of the cushion 12 and a second bushing as a bottom bushing 48 is provided at the bottom end 18 of the cushion 12. The front and bottom bushings 46, 48 can retain, fix, contain, restrain, hold, maintain, or otherwise couple the spring 44 within the cushion 12. The bushings provide for holding the spring 44 in place within the cushion 12. Additionally, the bushings can provide a soft or smooth contact for the line 22, such as a rubber bushing, which can improve lifetime for the line 22 and minimize stress on the line 22 during tensioning.

The spring 44 can be used to maintain the shape of the ear adapter assembly 10, or can be used to restore the ear adapter assembly 10 to its original position when the line is untensioned, released, unfixed, unclasped, opened, or the like. More specifically, the spring 44 can be used to maintain and return the ear adapter assembly 10 to an initial position after use. In this way, it should be understood that the spring 44 can operate similar to a controller, controlling the mode of the ear adapter assembly 10, such that the position, size or length, and spring constant for the spring 44 can be used to control adjusting of the ear adapter assembly 10. It should be understood that the controller need not be a spring 44, but can be any suitable element used to control the mode of the ear adapter assembly 10 as discussed herein.

Specifically, there are four elements where operation of any one element can affect one or more other elements. The four elements are the cushion 12, the spring 44, the line 22, and the clasp 30. The cushion 12, as discussed herein, provides for opposing ear deformation during the use of earwear, eyewear, or both. Since the cushion 12 can have different types of materials, material densities, or varying sizes or shapes, it is important that the user can controllably vary the position, shape, or size of the cushion 12 to provide comfort during varying uses or with varying eyewear or earwear. For example, a firmer cushion 12 will be somewhat denser and have a smaller initial size as compared to that of a softer type of cushion. Therefore, it is desirable that the ear adapter assembly 10 provide for tailoring the cushion 12 to the user regardless of the cushion 12 being used. Furthermore, the cushion 12 can operate similar to the spring 44 in that the cushion 12 is compressible and resist compression with a relatively low spring constant to return to its original shape.

The line 22 extends through the interior of the cushion 12, and can extend at least partially through the spring 44 or controller. Varying the length of the line 22 extending through the cushion 12, as shortening or lengthening the line 22, provides for varying the shape of the cushion 12. For example, a shorter line 22 or shortening thereof results in a smaller cushion 12, due to compression of the cushion 12, which can provide for a firmer fit. Similarly, a longer line 22 or lengthening thereof can result in a wider or enlarge cushion 12, which can provide for a softer fit.

The spring 44 can modulate or vary the amount of compression or expansion of the cushion 12. The spring 44 operates by providing opposition along the tensioned line 22. Thus, when the spring 44 is more compressed, it provides a greater expansive force resisting against the compression of the cushion 12 and maintains the shape of the cushion 12 via the clasp 30. When the spring 44 is less compressed, there is less of an expansive force resisting compression of the cushion 12. In this way, the spring 44 can be used to resist the compression and provide an expansive force, which can be used to return the cushion 12 to an initial position after use, or maintain a current compressed position by resisting further compression of the cushion 12. It should be understood that the spring 44 and line 22 may be replaced with an elastic or stretchable line 22 that servers to function as both the line 22 and the spring 44 providing the resistive force.

The clasp 30 provides for securing along the line 22, at the cushion 12, or both for securing a position of the spring 44. The clasp 30 provides for holding the spring 44 and the cushion 12 in the compressed position to effectively shorten the line 22, as well as provides for effectively lengthening the line 22 and decompressing the spring 44 and cushion 12 when the clasp 30 is disengaged.

Thus, compression or decompression of the spring 44 or controller can be used to adjust the tension on the line 22, which can be used to control attachment or unattachment of the line 22 to the eyewear, as well as a position and shape for the cushion 12. Furthermore, the spring 44 or controller can be used to adjust the form of the cushion 12. As the clasp 30 resists movement of the cushion 12 under tension of the line 22, movement of the clasp 30 towards the shorter length of line 22 within the cushion 12 can tension or compress the spring 44, which resists compression of tensioning of the line 22 or cushion 12. Similarly, movement of the clasp 30 towards the longer length of the line 22 within the cushion 12 releases the tension on the spring 44 and provides for decompression of the spring 44. In this way, the spring 44 generates the source of the tension on the line 22, which provides for returning the cushion 12 to an initial or expanded position after sustaining the shape change of the cushion 12 when secured with a fastener. For example, as the tension or compression of the line 22 is increased, the curvature of the cushion 12 can increase, conforming to the shape of the wearer's ear. In this way, adjusting the tension of the controller can provide for adjusting a mode of the line 22 (tensioned or untensioned), a mode of the eyewear fastener (such as the ring 26) as fastened or unfastened to the eyewear, or a mode of the cushion 12 as a shape of the cushion 12, which can be adjusted to shape to the user's ear. Thus, adjusting the clasp's position can provide for adjusting the mode of the ear adapter assembly 10 by adjusting the tension on the line 22. Furthermore, the clasp 30 can be used to secure the mode of the controller, securing the current position of the eyewear assembly 10, such as tensioned or untensioned, the fastener 26 being fastened or unfastened, or the particular shape of the cushion 12. It is further contemplated that the compression of the spring 44 can be used to tension the line 22. Specifically, the spring 44 operates similar to a 'backbone' or 'spine' for the ear adapter assembly 10, providing both stiffness and moderate flexion to maintain the overall shape of the cushion 12, while permitting flexion of the cushion 12 to conform to a user's ear.

A cover 50 can be provided around the cushion 12. The cover 50 can be made of a soft material, suitable to contact against a user's skin on the user's ear or head. In another non-limiting example, the cushion 12 can include a covering, casing, fillable support, sack, sleeve, or the like, filled with a cushioning material such as a soft or deformable material. The covering is preferably made of a washable material, facilitating cleaning for multiple usages. Additionally, the cover 50 is preferably of a washable material or one that is conducive to cleaning with liquid agents or other treating chemistry. Furthermore, the cover 50 can be colored, decorated, or otherwise marked suitable to the taste of a user, or can include images or markings to identify the ear adapter assembly 10, for example.

Figure 3:
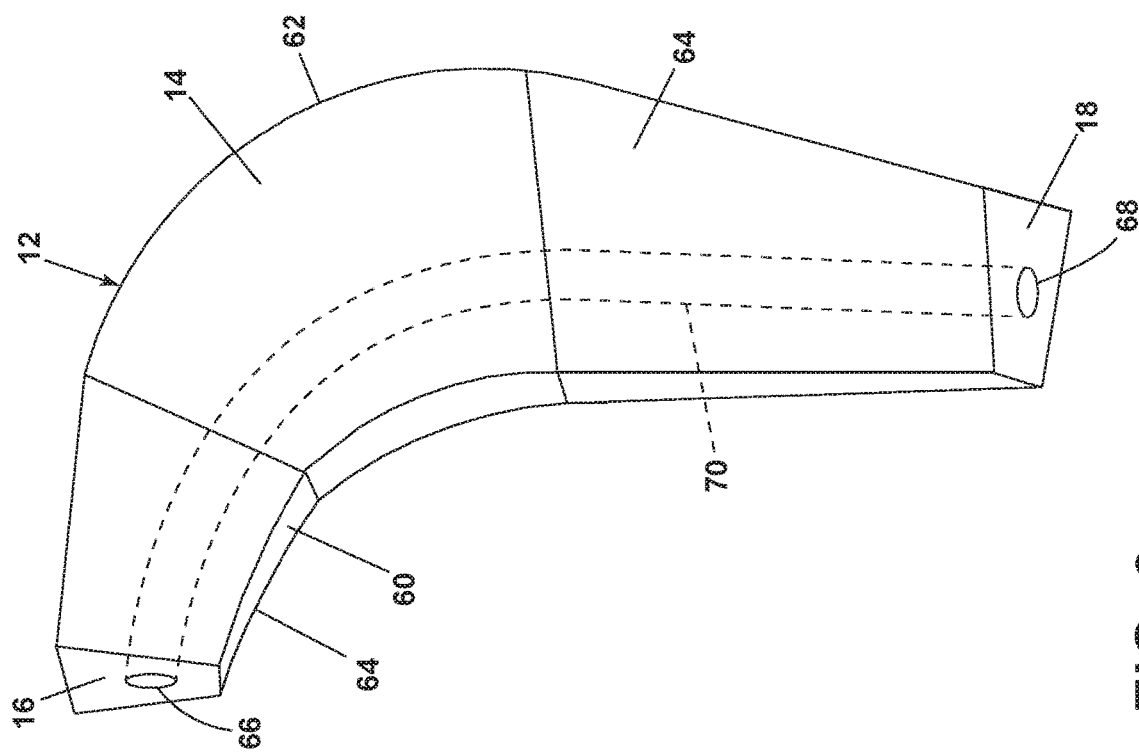
FIG. 3 is an isometric view of the cushion of the ear adapter assembly of FIG. 1.

Referring now to FIG. 3, the body 14 of the cushion 12 can include an interior side 60 configured to abut the user's ear at the user's head, an exterior side 62 opposite the interior side 60, and opposing sidewalls 64 extending between the interior side 60 and the exterior side 62. The interior side 60, exterior side 62, and sidewalls 64 terminate at the front end 16 and the bottom end 18. The cushion 12 can include a curved geometry, contouring, shaping, or the like, such that the front end 16 and the bottom end 18 can define planes substantially orthogonal to one another, while it is contemplated that such planes can vary from orthogonal to one another by forty-five degrees or more. Such variation can be suitable for tailoring the cushion 12 to the unique, variable shapes of different users' ears. The interior side 60 can be adapted to insert along the ear of a user. As such, the sidewalls 64 can be adapted to rest between the side of a user's head and a pinna portion of the user's ear. In this sense, the cushion 12 allows for or permits interchangeable use relative to either ear or either side of a user's head. Therefore, the ear adapter assembly 10 can be interchangeable between a user's left and right ears. Alternatively, the cushion 12 can be adapted or configured to be worn, formed, or contoured for a specific ear or side of a user's head (e.g. right side or left side). The front and bottom ends 16, 18 can have a trapezoidal geometry more common to the typical ear shape, while alternative geometries are contemplated, such as square, oval, wave-like, or rectangular in non-limiting examples. Additional intermediate cross-sections of the cushion 12 can further have a trapezoidal or wedge-like geometry, yet varying therefrom, such as having curved or rounded sides, while a myriad of variations are contemplated.

A first aperture as a front aperture 66 can be provided in the front end 16 of the cushion 12, continuing through the cushion 12 as a conduit 70 to a second aperture as a bottom aperture 68 at the bottom end 18 of the cushion 12. The conduit 70, the front aperture 66, and the bottom aperture 68 collectively provide for insertion of the curved channel 40, spring 44, and the line 22 of FIG. 2. Alternatively, in an example where the cushion 12 consists of a compressible material, such as foam, the curved channel 40 can be inserted through or integral with the cushion 12, without the need for forming the conduit 70 into the cushion 12.

Figure 4:
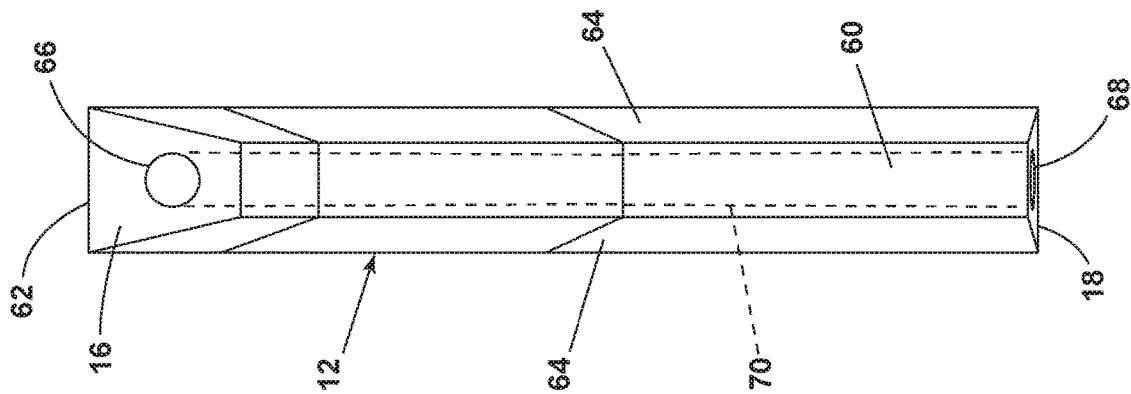
FIG. 4 is a front view of the cushion of FIG. 3.

Referring now to FIG. 4, the sidewalls 64 of the cushion 12 can be tapered, such that the interior side 60 has a smaller width than that of the exterior side 62. As such, the interior side 60 can have a smaller cross-sectional area than that of the exterior side 62. In this way, the shape of the cushion 12 is configured to conform to the area between a user's ear and a user's head, while providing suitable cushioning.

Figure 5:
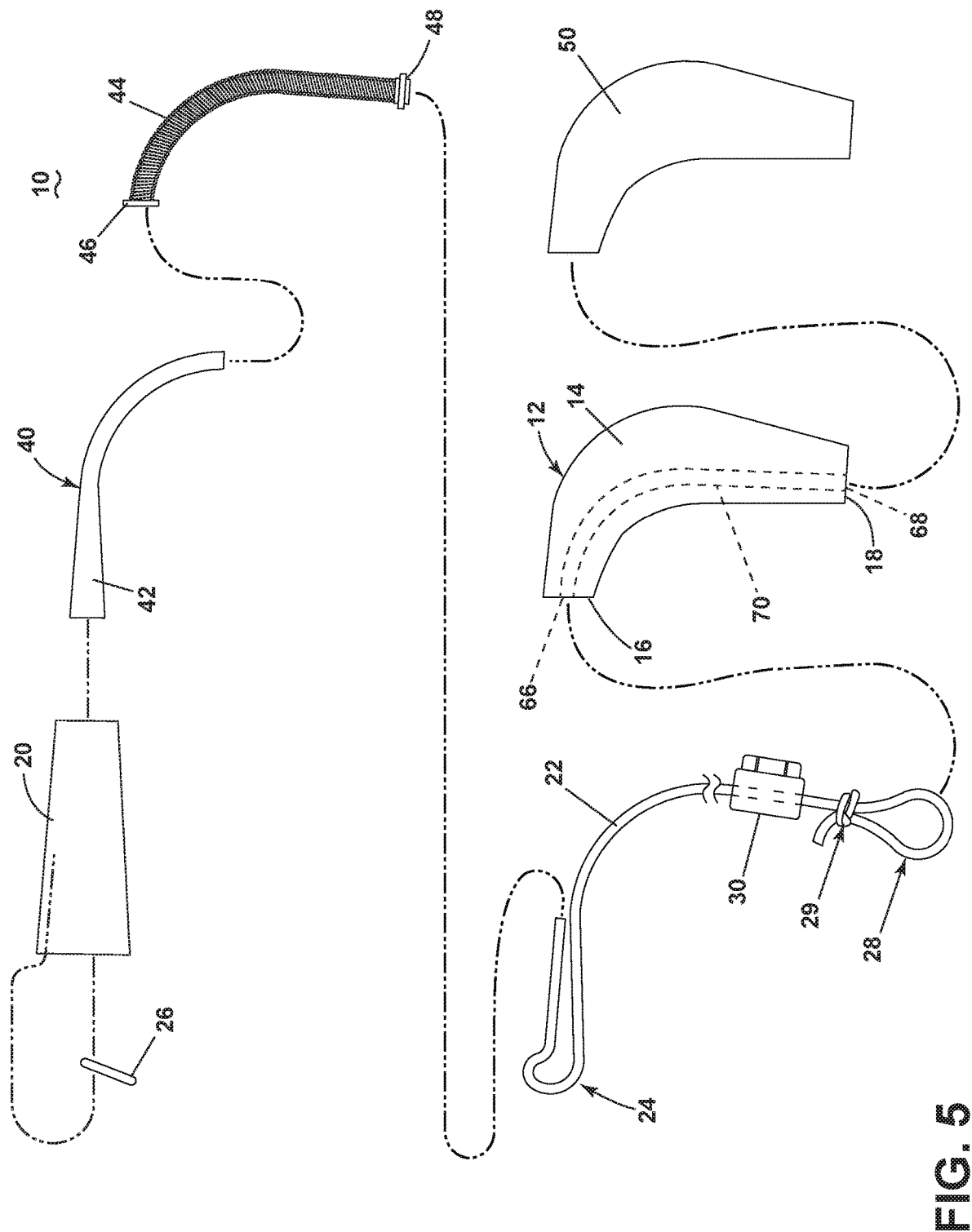
FIG. 5 is an exploded view of the ear adapter assembly of FIG. 1.

Referring now to FIG. 5, assembly of the ear adapter assembly 10 can be appreciated. It should be understood that the exploded view as shown should not be limiting as an order of assembly, but as one potential arrangement for assembling the ear adapter assembly 10. The spring 44 having the front and bottom bushings 46, 48 can be provided around at least a portion of the curved channel 40, such as by sliding the spring 44 over the curved channel 40. As shown, the spring 44 would extend along the curved channel 40 with the front bushing 46 positioned just prior to the flared channel 42. In an alternative example, the front bushing 46 can be omitted if the curved channel 40 and the flared channel 42 are connected such that the shape of the securing element 20 provides the terminal extent for the spring 44. The combined spring 44 and curved channel 40 can be inserted into the front aperture 66 of the cushion 12, while it is contemplated that the curved channel 40 can be inserted at the bottom aperture 68.

The line 22 can be threaded through the combined spring 44, curved channel 40, and cushion 12, until the line 22 extends out of the flared channel 42 of the curved channel 40 and extends out of the bottom end 18 of the cushion 12. The eyewear ring 26 can be threaded or otherwise affixed onto the line 22. The line 22 can be attached to the exterior of the flared channel 42 of the curved channel 40 to form the loop 24, while an interior attachment is also contemplated. The securing element 20 or other suitable fastener can be used to secure the line 22 to the flared channel 42.

The clasp 30 can be threaded along the line 22 adjacent the bottom end 18 of the cushion 12, such that the line 22 is routed through the clasp 30 providing slidable movement of the line 22 relative to the clasp 30 or the clasp 30 relative to the line 22. The knot 29 can optionally be pre-formed in the line 22 with the clasp 30, or can be completed after assembly. The cover 50 can be provided around the cushion 12 to protect the cushion 12, to provide ornamentation to the cushion 12, to form a hygienic and cleanable skin contact surface, to contain one or more shape-adjusting pieces (see FIG. 9) to form the cushion 12, or to serve as a convenient accessory attachment point for the ear adapter assembly 10.

Figure 6:
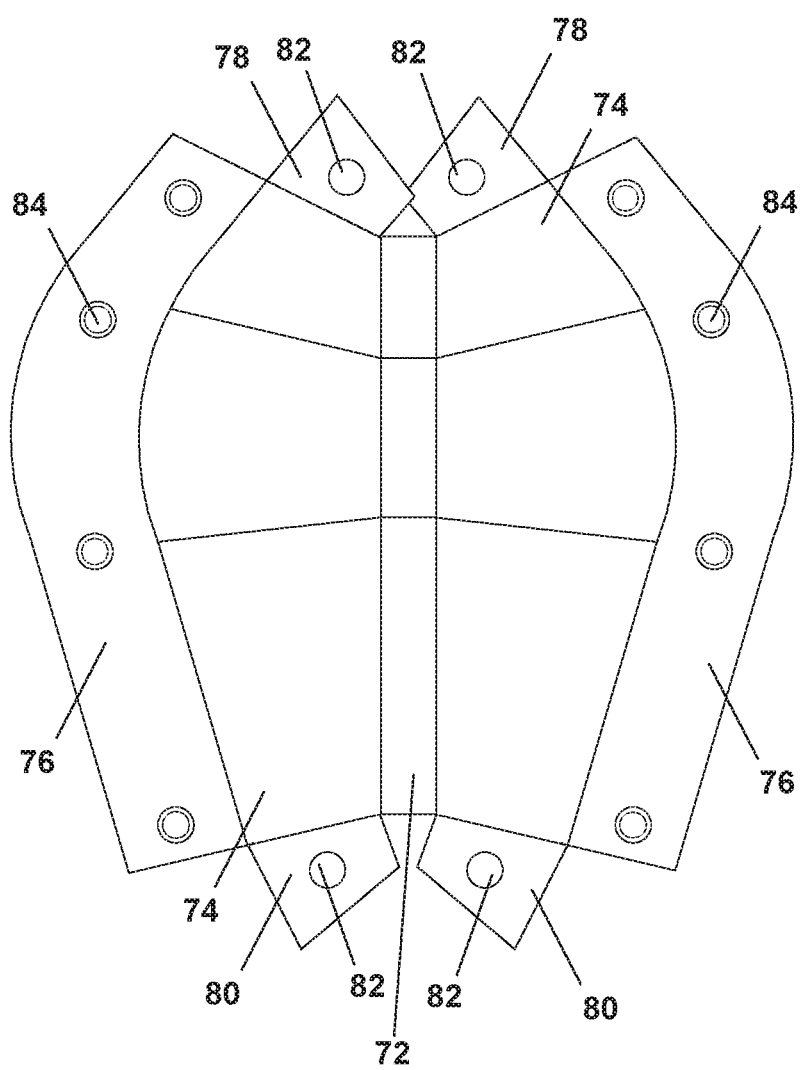
FIG. 6 is a view of a cover in an unassembled position for covering the cushion of FIG. 4.

Referring now to FIG. 6, the cover 50 is shown in a flattened position as a removable cover, while it is alternatively contemplated as affixed to the cushion 12. The cover 50 can include an interior side portion 72 sized and shaped complementary to the interior side 60 of the cushion 12. A pair of opposing side portions 74 extend from the interior side portion 72 and can be sized and shaped complementary to the sidewalls 64 of the cushion 12. Similarly, a pair of exterior side portions 76 can extend from the side portions 74 opposite of the interior side portion 72 and can be sized and shaped complementary to the exterior side 62 of the cushion 12. A pair of front end portions 78 and a pair of bottom end portions 80 each extend from opposite ends of the side portions 74, and can be sized and shaped complementary to the front end 16 and the bottom end 18 of the cushion 12, respectively. Openings 82 can be provided in the front end portions 78 and the bottom end portions 80 complementary to the front aperture 66 and the bottom aperture 68 of the cushion 12. A set of fasteners 84 can be provided on the exterior side portions 76. The fasteners can be snap-buttons, for example, while any suitable fastener is contemplated, such as buttons, snaps, tags, clasps, hook and loop fasteners, or adhesives in non-limiting examples.

Fastening the cover 50 about the cushion 12 can include positioning the interior side 60 of the cushion 12 along the interior side portion 72 of the cover 50. The cover 50 can be wrapped about the cushion 12, positioning the side portions 74 against the sidewalls 64 of the cushion and aligning the exterior side portions 78 along the exterior side 62 of the cushion 12. In doing so, the front end portions 78 can align against the front end 16 of the cushion 12 and the bottom end portions 80 can align against the bottom end 18 of the cushion 12. The fasteners 84 can be secured to one another to secure the cover 50 about the cushion 12. The cover 50 can be easily and readily removed by un-fastening the fasteners 84 and removing the cover 50 from the cushion 12, such as for washing, decorating, or replacing.

Figure 7:
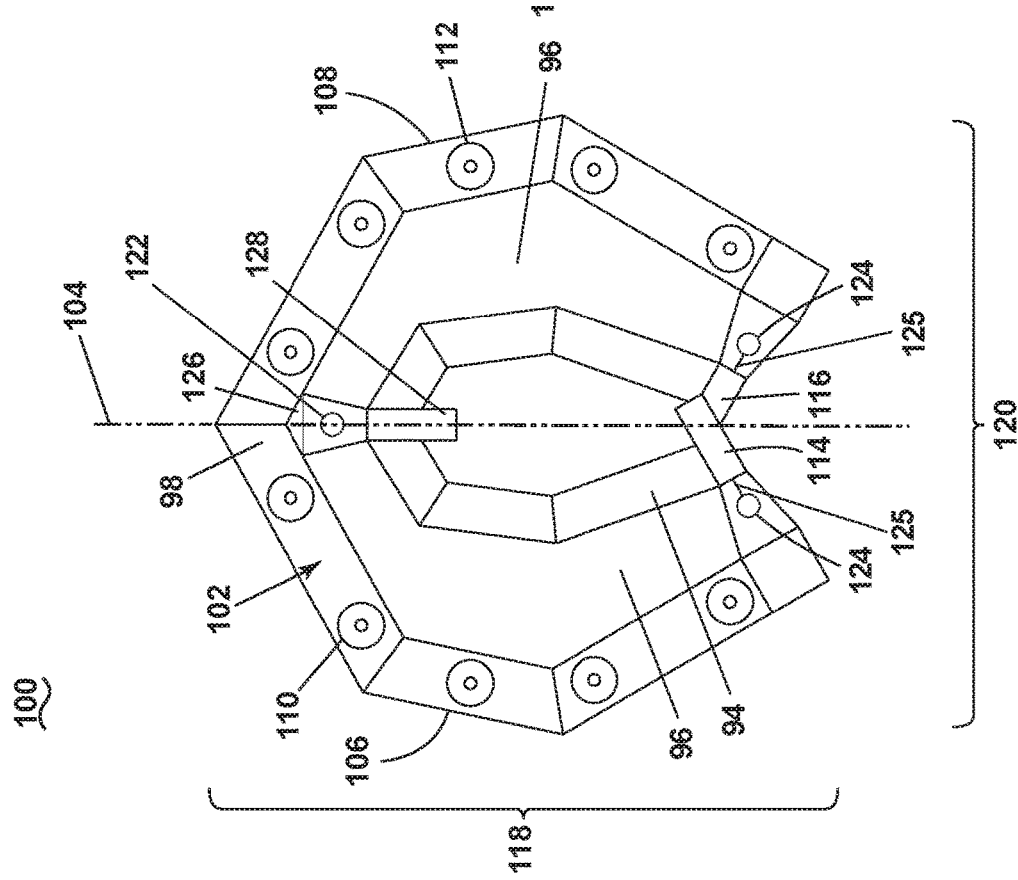
FIG. 7 is a view of another exemplary cover in an unassembled position for covering the cushion of FIG. 4.

Referring now to FIG. 7, another exemplary cover 100, which can be used as the cover 50 as depicted in FIGS. 2-5, for example, can include a flat body 102. The cover 100 can be substantially symmetric about a longitudinal centerline 104, while variations are contemplated to facilitate fastening of the cover 100 about a cushion, such as the cushion 12 of FIGS. 1-5. The cover 100 includes a left side 106 and a right side 108, separated by the centerline 104, while it should be appreciated that left and right are not limiting of which side of the user's head the ear adapter assembly 10 is worn. Each side 106, 108 can include an interior portion 94, a side portion 96, and an exterior portion 98. The interior portions 94 are sized to cover the interior side 60 of the cushion 12, the side portions 96 are sized to cover the sidewalls 64 of the cushion 12, and the exterior portions 98 are sized to cover the exterior side 62 of the cushion 12.

Each side 106, 108 can include a set of complementary set of fasteners, with a set of male fasteners 110 on the left side 106 and a set of female fasteners 112 on the right side 108 adapted to couple to one another. The fasteners 110 on the left side 106 can be connected to the fasteners 112 on the right side 108 to form a shape for the cover 100 shaped and adapted to surround the cushion 12 as described herein. It should be appreciated that the particular arrangement of the fasteners 110, 112 can vary, but serves to join the left side 106 to the right side 108 in order to cover the cushion 12 as described herein. Additionally, the left side 106 can include a first tab 114 and the right side 108 can include a second tab 116. Alternatively, the tabs 114, 116 can be optional, such as removed, non-user operable, or sewn into the remaining portions of the cover 100. In an additional example, the tab and receptacle can be made of a hook-lock connector or are magnetic to secure to a support along the interior side 60 of the cushion 12, as shown in FIG. 4, opposite of the fasteners 110, 112, which can be positioned along the exterior side 62. It should be appreciated that the fasteners 110, 112, or tab 114 and receptacle 116 are preferably positioned at an area where they do not contact a user's ear or head when the ear adapter assembly 10 is used, to prevent any unwanted deformation, discomfort, or pain from the ear adapter assembly 10 itself. As such, it may be desirable to have different fasteners at different positions on the cover 100. Such suitable different fasteners can include, in non-limiting examples, one or more snaps, ties, zippers, buttons, lacing, hooks, loops, or any other attachment or non-permanent closure.

The cover 100 can include a front opening 122, and a set of bottom openings 124. The front opening 122 can be adapted to be positioned at the front aperture 66 of the cushion 12 when the cover 100 is provided over the cushion 12. Similarly, the bottom openings 124 can be adapted to be positioned at the bottom aperture 68. A slit 125 can be provided at the bottom openings 124 to facilitate insertion of elements through the bottom openings 124, such as the line 22 of FIG. 1. It is further contemplated that a similar slit 125 can be provided at the front opening 122. Additionally, the portion of the side portions 96 containing the front opening 122 and the bottom openings 124 can be sized complementary to the front end 16 and the bottom end 18 of the body 14, respectively. A gap 126 can be formed as a cut-out of the cover 100 provided between the side portion at the front opening 122 and the exterior portion 98, permitting flexion of the cover 100 at that area. Additionally, another tab 128 can be provided at the interior portion 94 adjacent the front opening 122. The tab 128 can be folded over or sewn to the other portions of the cover 100, for example. While shown as having a seam at the top area of the cover 100, it is contemplated that the seam can be provided anywhere along the cover 100, as may be desirable. Preferably, the seam would be positioned away from the user's skin or body surface, to prevent any potential irritation.

Furthermore, the cover 100 can have a height 118 and a width 120. The height 118 and the width 120 can be tailored to a particular size of support, such as a small, medium, large, tall, short, wide, thin, or any other suitable denomination or sizing. Due to the unique nature of a user's ear, it can be desirable to have different sizes for the ear adapter assembly 10, as well as different covers 100 adapted for use with the different ear adapter assemblies 10.

The cover 100 can be made of cloth, or other suitable material desirable to a user. Suitable materials can include materials that are comfortable to a user, or are suitable for washing and maintenance, while any suitable material is contemplated. While fasteners 110, 112 are shown and described, aspects of the disclosure can be included wherein alternative fasteners can be utilized. For example, aspects of the disclosure can be included wherein the cover 100 is bonded, attached, connected, or the like, utilizing zippers, hook and loop connectors, adhesives, latches, glue, straps, or the like. In yet another non-limiting aspect of the disclosure, the cover 100 can comprise an expandable cloth material without fasteners at all, wherein the cover 100 can be, for instance, stretched over the underlying structure without the need to fasten.

Figure 8:
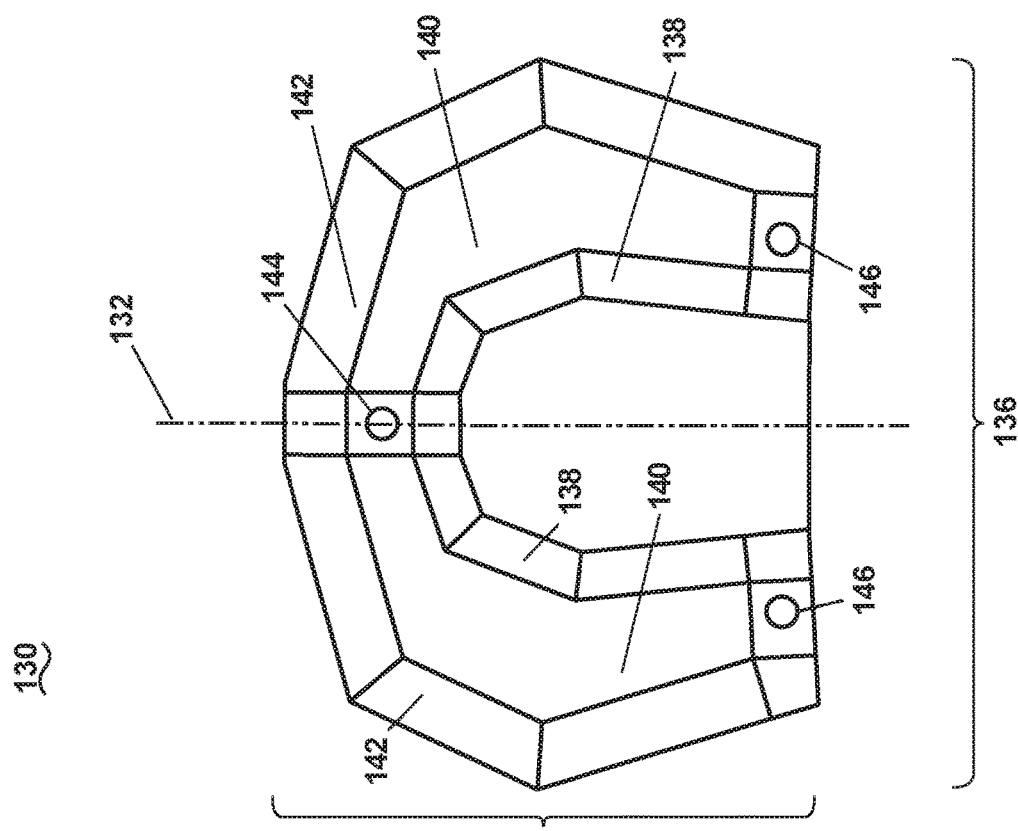
FIG. 8 is a view of yet another exemplary cover in an unassembled position for covering the cushion of FIG. 4.

Referring now to FIG. 8, another alternative cover 130 is shown, having a symmetric organization about a longitudinal centerline 132, having an interior portion 138, a side portion 140, and an exterior portion 138 on both sides of the cover 130. The interior portion 138 can be sized to cover the interior side 60 of the cushion 12, the side portion 140 can be sized to cover the sidewalls 64 of the cushion 12, and the exterior portion 142 can be sized to cover the exterior side 62 of the cushion 12. The exterior portions 142 can be adapted to couple to one another, to secure around the cushion 12. A front opening 144 can be positioned to arrange over the front aperture 66 of the cushion 12 and a set of bottom openings 146 can be positioned to arrange over the bottom aperture 68 of the cushion 12.

Furthermore, a height 134 for the cover 130 is lesser than that of the cover 100 in FIG. 6, while a width 136 is greater than that of the cover 100 in FIG. 6, illustrating one example of the sizing variability and fastener arrangement variability of the cover 130.

It should be understood that there are a myriad of different possible covers 50, 100, 130, having different sizes, shapes, fastening features, as well as ornamentation or coloring. Such covers 50, 100, 130 can be particularly tailored to the particular cushion 12, ear adapter assembly 10, or the particular user, as may be desirable or beneficial.

Figure 9:
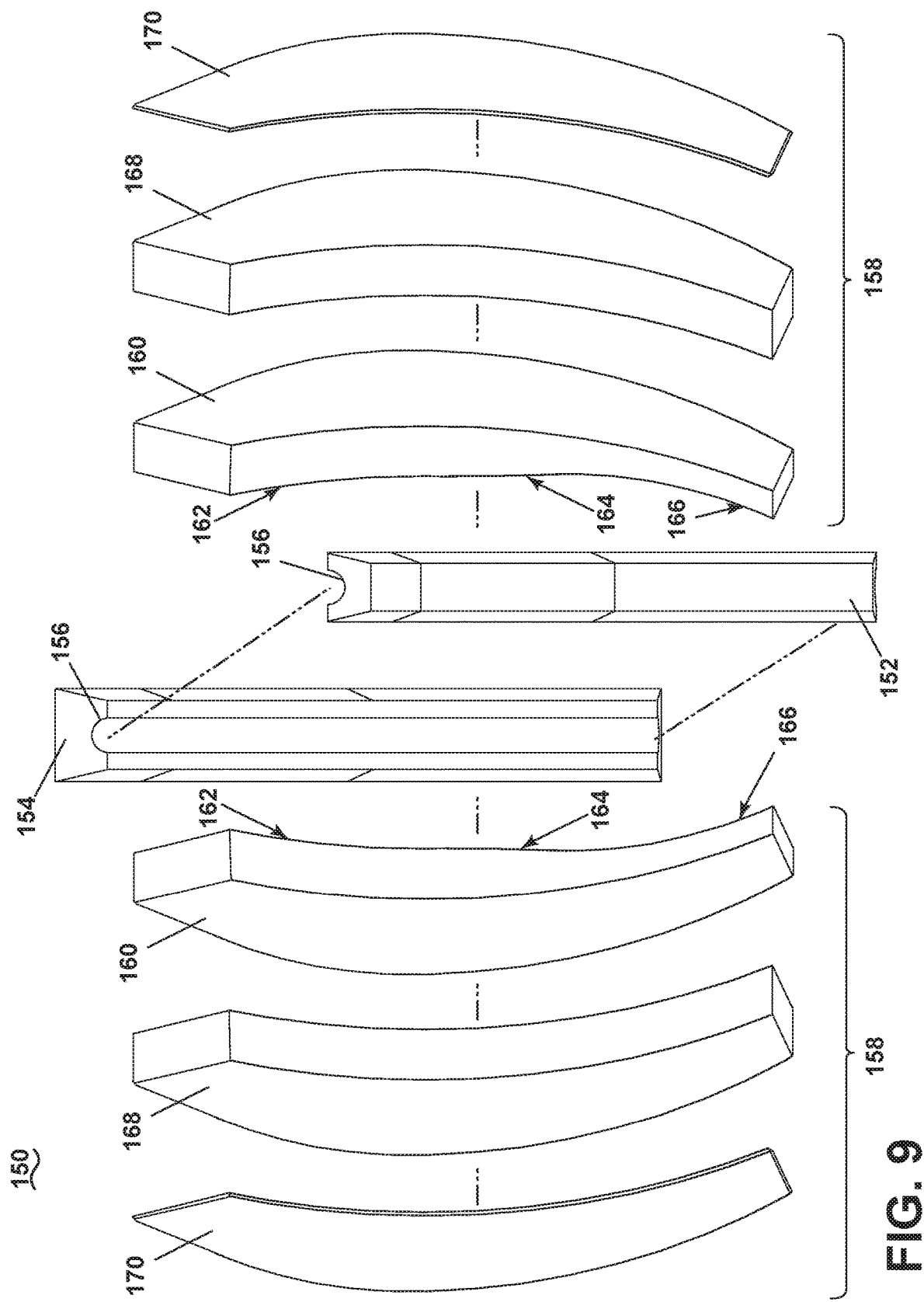
FIG. 9 is an exploded view of the cushion of FIG. 4 including separable cushion pieces for forming the cushion.

Referring now to FIG. 9, an exemplary cushion assembly 150 is shown, which can be used as the cushion 12 of FIGS. 1-5, for example. The cushion assembly 150 can include an interior cushion portion 152 and an exterior cushion portion 154. Each portion 152, 154 can include a groove 156 configured to abut the curved channel 40 or the spring 44 inserted into the cushion 12. The interior portion 152 and the exterior cushion portion 154 are configured to abut one another to align the grooves 156 to form the conduit 70 described in FIG. 3. In an alternative example, the interior and exterior cushion portions 152, 154 can be formed as a single element, with portion of the ear adapter assembly 10 insertable through the unitary portions 152, 154. In an alternative example, portions 152 and 154 can be unitary, having a slit formed in the side of the unitary portion for inserting the curved channel 40 or the spring 44.

The cushion assembly 150 can further include a set of side cushions 158 adapted to abut the sides of the interior and exterior cushion portion 152, 154. The set of side cushions 158 can include a variety of different sizes and shapes. In this way, a user can assemble the cushion assembly 150 to tailor to the particular shape of the user's ear, as ear shapes can significantly vary among users. This modular cushion assembly provides for specific tailoring of the cushion assembly 150, and therefore the ear adapter assembly 10, to fit any user's ear.

A first set of side cushions 160 can include a varying thickness, being wider toward a front 162 of the cushion 160 and including a transition portion 164 transitioning to a thinner thickness toward the bottom 166, as compared to the top 162. While shown as having a wider thickness toward the top 162, it is contemplated that the wider thickness can be positioned anywhere along the first set of side cushions 160, or can have multiple or discrete thickened portions. A second set of side cushions 168 can include a constant thickness. A third set of side cushions 170 can be thin, used to slightly vary the thickness of the cushion assembly 150 to very specifically tailor the thickness of the cushion assembly 150. The third set of side cushions 170 can be used for fine adjustment, as they can be very thin and only adding or removing a slight thickness for the overall cushion assembly 150. Assembly of the cushion assembly 150 can be completed by fastening the cover 50 about the set of cushions, for example.

It should be appreciated that the cushion assembly 150 as shown is exemplary, and only illustrates a few examples of cushions. It should be understood that a myriad of cushion sizes, shapes, thicknesses, stiffnesses, materials are possible, providing for a plurality of combinations thereof. The cushion portions can be stackable in order to vary and tailor the specific shape of the cushion assembly 150 to the user. Such as assembly 150 can be symmetric or asymmetric, accounting for tilt adjustment, providing for tailoring to a wider range of ear shapes. In this way, the cushion assembly 150 can be wholly customizable to tailor to the varying ear sizes of potential users. Such customizability provides for creating the most comfortable combination for the user based upon the user's specific ear size and shape. Alternatively, it is contemplated that the cushion 12 is formed as a single member, and need not be a modular assembly. Furthermore, such customizability can provide for tailoring the ear adapter assembly 10 to opposing ears on a user's head, which can be unique in comparison to one another.

Figure 10:
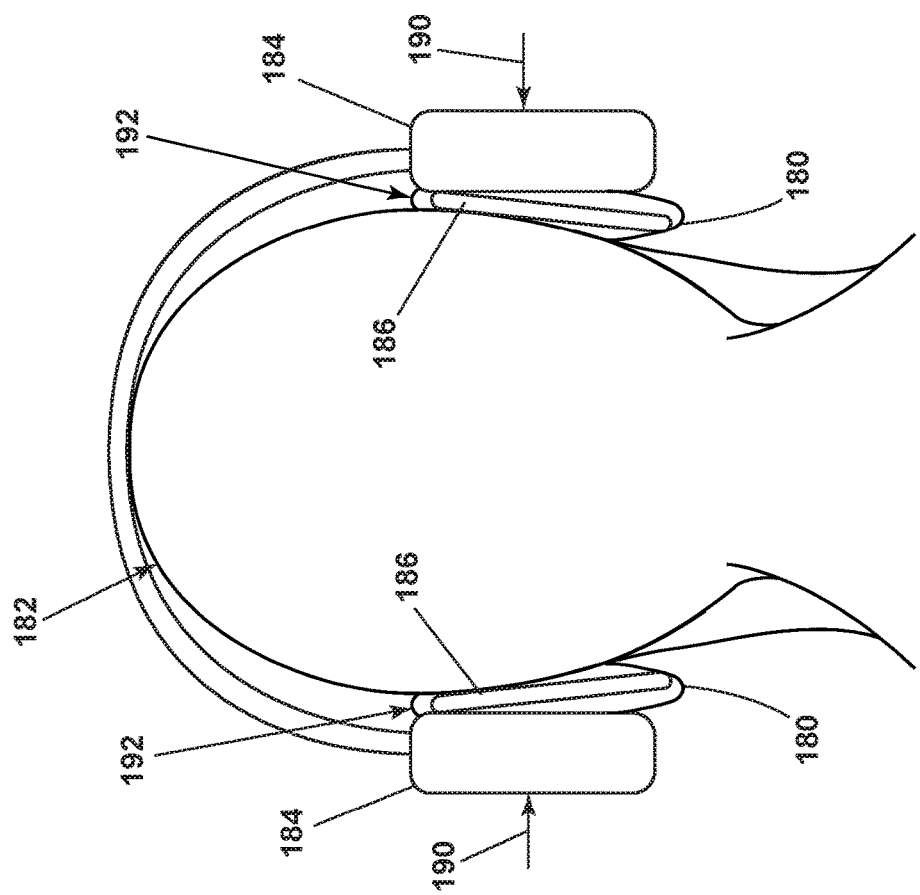
FIG. 10 is a rear view of a user's head showing a compressive force from earwear applied against the user's head.

Referring now to FIG. 10, rear view of a user's head 182 shows concurrent use of earwear, shown as headphones 184, and eyewear, shown as a frame or eyewear temple 186 of a pair of eyewear glasses. The eyewear temple 186 positions behind a pinna portion 180 of a user's ear, between the user's head 182 and the pinna portion 180 of the user's ear. The headphones 184 affix to the exterior of the user's head 182 at the user's ear. The headphones 184 provide a compressive force 190 against or lateral to the user's head 182 to secure the headphones 184 on the user's head 182 over the user's ears. The compressive force 190 of the headphones 184 can result in the deformation 192 or deflection of a user's ear about the eyewear temple 186. Such deformation 192 or deflection can cause discomfort or pain for the user. The application of the compressive force 190, concurrent with wearing of the eyewear temple 186, results in an unbalanced torque 188 (see FIG. 11) being applied to the user's ear, causing a buckling of the pinna portion 180 in the vicinity of the eyewear temple 186. Such a buckling can cause a pinching of nerves within the user's ear, which can cause discomfort.

Figure 11:
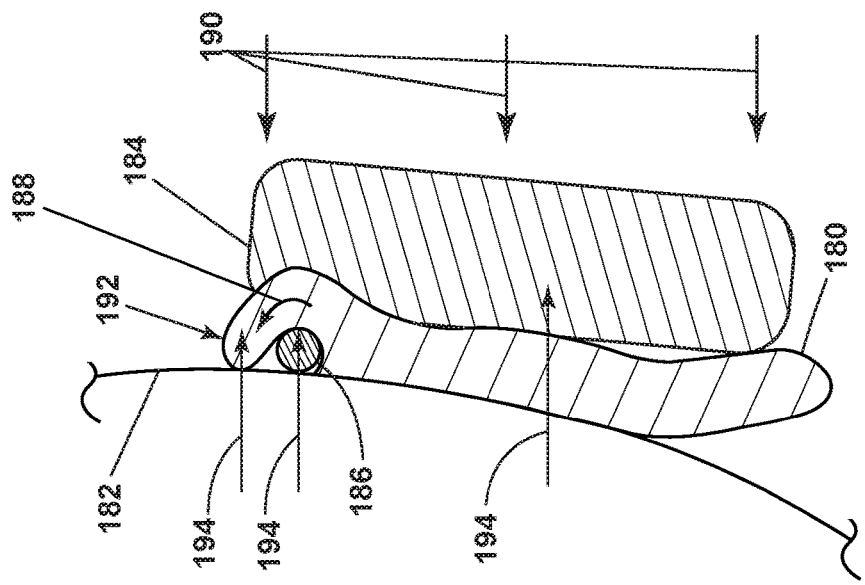
FIG. 11 is a section view of a pinna portion of user's ear of FIG. 8, showing deformation of the user's ear during concurrent use of earwear and eyewear.

Referring now to FIG. 11, a section view better illustrates the deformation 192 or buckling of the pinna portion 180 of the user's ear resultant of the compressive force 190. The compressive force 190 of the headphones 184 results in deformation 192 of the user's ear about the eyewear temple 186 of the user's glasses. A resistive force 194 is provided from the user's ear and the user's head 182, opposite of the compressive force 190. The cartilage shape of the pinna portion 180 of the user's ear, for example, can at least partially provide the resistive force 194. The compressive force 190 of the headphones 184 is greater than that of the resistive force 194, resulting in the torque 188 on the user's ear about the eyewear temple 186. The torque 188 results in the deformation 192 or buckling of the user's ear about the eyewear temple 186. Such deformation can cause discomfort or pain for a user.

Figure 12:
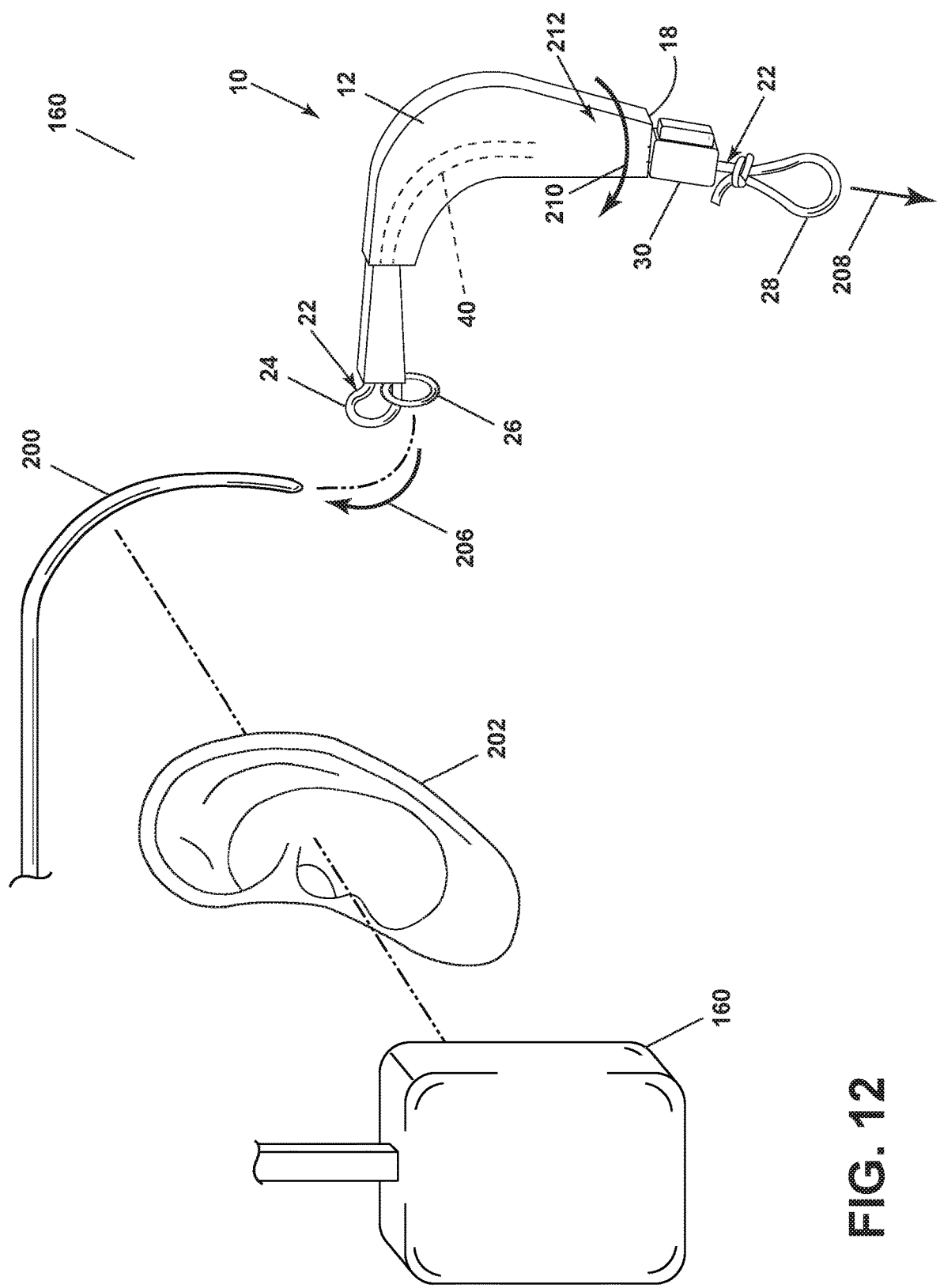
FIG. 12 is an exploded view of an assembly sequence for attaching and positioning the ear adapter assembly of FIG. 1 at the pinna portion of the user's ear.

Referring now to FIG. 12, an exploded view of the ear adapter assembly 10, an eyewear temple 200, a pinna portion 202 of a user's ear, and a portion of a pair of headphones 204 is shown, depicting installation of the ear adapter assembly 10. As the eyewear temple 200 is worn behind or between the pinna portion 200 of the ear and the head, the headphones 204 are provided on the exterior, lateral area of the pinna portion 200 of the ear. Such a combination can result in the painful ear torque or compression as described in FIGS. 10 and 11.

The earwear ring 26 of the ear adapter assembly 10 can be slid along the eyewear temple 200 of the eyewear, illustrated by arrow 206, until the cushion 12 is positioned and substantially aligned with the user's ear. Once suitably positioned, the user can pull the line 22 at the adjustment loop 28, illustrated by arrow 208, retracting the line 22 at the loop 24, and pulling the eyewear ring 26 at least partially within the securing element 20 to tighten the eyewear ring 26 around the eyewear temple 200. Tightening of the line 22 can be secured with the clasp 30. In this way, pulling the line 22 at the adjustment loop 28 secures the ear adapter assembly 10 to the eyewear temple 200 and secures the position of the ear adapter assembly 10 between the pinna portion 202 of the user's ear and the user's head. The clasp 30 is used to secure the position and tension of the line 22 at the bottom end 18 of the ear adapter assembly 10.

Additional tightening or tensioning of line 22 at the adjustment loop 28 can be used to further conform the cushion 12 about the pinna portion 200 of the user's ear. Additional tightening or tensioning of the line 22 can provide for securing the eyewear loop 24 to the temple of the eyewear 200, and/or can provide for squeezing, shaping, or compressing the cushion 12 at or near the bottom end 18, below the internal curved channel 40, which can form the bottom end 18 of the cushion 12 inwardly, as illustrated by arrow 210. In this way, the shape or density of the cushion 12 can be modified to conform more to the user's ear, tailoring the cushion 12 to the lateral curvature of the user's ear. The shape can be conformed relative to a centerline of the channel 44, following the curvature of the user's ear, as opposed to merely positioning the ear adapter assembly 10 at the ear adjacent the eyewear temple 200. Such shaping can provide for increasing local resistive forces to counteract greater local compressive forces or movement forces generated by the earwear 160. More specifically, a greater tension on the line 22 draws the bottom end 18 of the cushion 12 closer to the bottom end of the curved channel 40. Such curvature of the cushion 12 can be the result of the curved channel 40 within the cushion 12, such as containing a pivoting portion (not shown), alternative more-flexible and less-flexible section along the channel 40, or simply terminating prior to the bottom end 18, as shown, in non-limiting examples. The early termination provides for a flexible portion 212 of the ear adapter assembly 10 that can conform to the user's ear, while the portion of the cushion 12 occupied by the curved channel 40 remains substantially rigid, with the curved channel 40 effectively forming a 'spine' or 'backbone' for the ear adapter assembly 10. Such an organization provides for ease of use by the user to conform the ear adapter assembly 10 to the specific shape of the user's ear, as well as provides for better securing the ear adapter assembly 10 to the user's ear.

Figure 13:
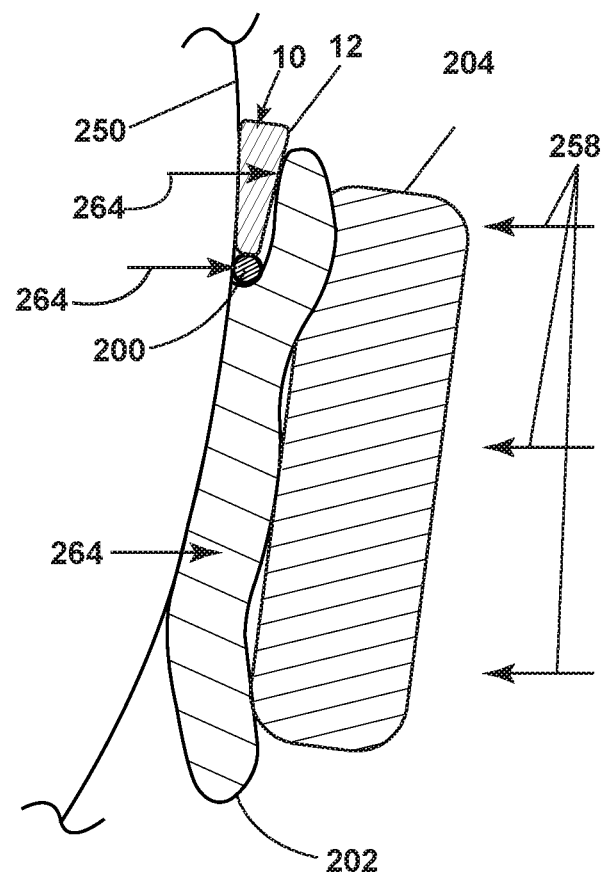
FIG. 13 is a section view of the pinna portion of the user's ear, utilizing the ear adapter assembly of FIG. 1 during concurrent use of earwear and eyewear.

FIG. 13 illustrates a sectional view of the combined ear adapter assembly 10, pinna portion 202, eyewear temple 200, and earwear shown as headphones 204 of FIG. 12. The ear adapter assembly 10 provides a normal force 264 (schematically shown with an arrow) opposite of a compressive force 258 provided by the headphones 204. The normal force 264 provided by the ear adapter assembly 10 is extended from the user's head 250 to counteract the compressive force 258 of the headphones 204. When the compressive force 258 of the headphones 204 is present, the ear adapter assembly 10 provides the normal force 264 to counter the torque of the compressive force 258, such that pivoting or deformation of the user's ear about the eyewear temple 200 is reduced or eliminated. Furthermore, the ear adapter assembly 10 occupies the space between the pinna portion 248 of the user's ear and the user's head, reducing the opportunity for deformation of the user's ear 86 into the now-occupied space. In this sense, the normal force 264 provided by the cushion 12, the ear adapter assembly 10, or a portion thereof, can oppose, resist, or counter the compressive force 258. In another sense, the cushion 12 or the ear adapter assembly 10 can reinforce, support, or back the pinna portion 202 of the user's ear to resist deforming about the eyewear temple 200. Reducing the deformation can reduce or eliminate the sensation of pain or discomfort with the user due to the compressive force of the earwear or the concurrent use of eyewear with earwear.

Figure 14:
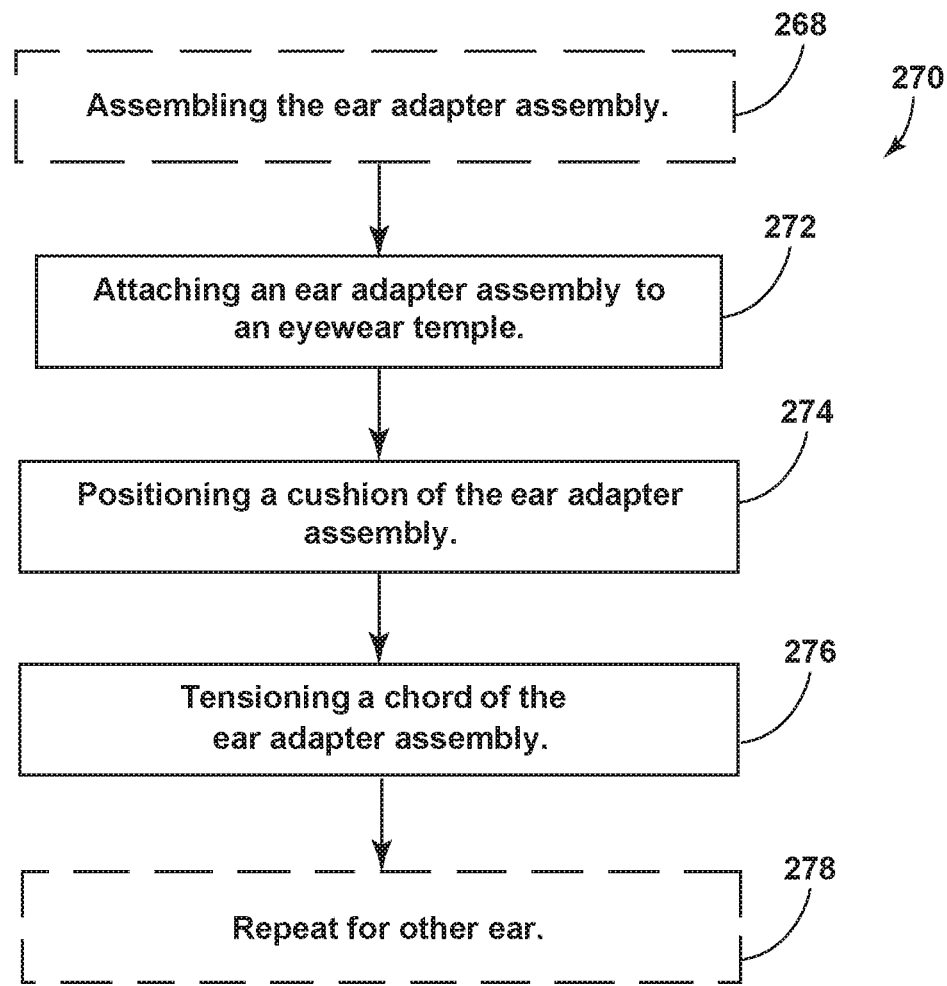
FIG. 14 is a flow chart detailing a method of distributing a force of earwear against a pinna portion of a user's ear.

Referring now to FIG. 14, a method 270 of distributing a force of earwear against a user's ear can include: at 268, optionally, assembling the ear adapter assembly; at 272, attaching an ear adapter assembly 10 to an eyewear temple; at 274, positioning a support, such as the cushion 12, of the ear adapter assembly 10; at 276, tensioning a line 22 of the ear adapter assembly 10; and at 278, optionally, repeating the method with another ear adapter assembly for the other ear on the other side of the user's head. It should be appreciated that portions of the method 270 as discussed are optional, and one or more portions can be added, removed, or reordered as may desirable for distributing a force of earwear against a user's ear.

At 268, the method can optionally include preparing the cushion 12 for the ear adapter assembly 10 or assembling the ear adapter assembly 10. For example, the user can combine one or more portions of the cushion 12, such as those described in FIG. 9, about the curved channel 40. The user can selectively add or remove one or more side cushions 158 until the sizing and shape of the cushion 12 is tailored to the particular user's ear. From here, the user can secure the cover 50 about the cushion 12 to assemble the ear adapter assembly 10. In this way, it should be appreciated that the cushion 12 can be a modular assembly which can be modified and tailored to fit the individual ear shape of the particular user. In one example, the cover 50 can include or serve as a sleeve, where not only does the cover 50 envelope the cushion 12, but also such that the eyewear temple of a user's glasses can be slid to hold the eyewear and the ear adapter assembly 10 together.

At 272, the ear adapter assembly can be the ear adapter assembly 10 as described herein. Additionally, the ear adapter assembly 10 can further include any of the additional elements as described herein. Attaching the ear adapter assembly 10 to an eyewear temple can include sliding the eyewear ring 26 around the temple of the eyewear, while it is contemplated that the line 22 can be positioned around the temple 200 of the eyewear. From here, a user can put on the eyewear, the ear adapter assembly 10, or the combination of the two. In doing so, the user can further position the ear adapter assembly 10 between the pinna portion of the user's ear and the user's head in a comfortable position seating the ear adapter assembly as desired.

At 274, the cushion 12 can be positioned between a pinna portion of the user's ear and the user's head, such as that shown in FIGS. 10 and 11. The position of the ear adapter assembly 10 can be varied based upon the position of the eyewear ring 26 along the temple 200 of the user's eyewear.

At 276, the line 22 can be tensioned to secure the cushion 12 against the user's ear. The user can depress the clasp 30 and slide the line 22, tensioning or tightening the eyewear ring 26 about the temple of the eyewear. This can be done by pulling the adjustment loop 28, for example. Additionally, the user can further pull the line 22 down and slide the clasp 30 against the bottom end 18 to deform or compress the cushion 12 to better conform to the curvature of the user's ear. The clasp 30 can be released to secure the position of the tensioned or tightened line 22, and therefore, the ear adapter assembly 10.

At 278, the process or method can be repeated for another ear adapter assembly 10 for the other ear on the other side of the user's head. When using eyewear in combination with earwear, such a combination commonly is applied to both of the user's ears. Therefore, it would be desirable to have two ear adapter assemblies 10, one for each ear.

The sequence depicted is for illustrative purposes only and is not meant to limit the method 270 in any way as it is understood that the portions of the method can proceed in a different logical order, additional or intervening portions can be included, or described portions of the method can be divided into multiple portions, or described portions of the method can be omitted without detracting from the described method.

The ear adapter assembly 10 as described herein and the method of distributing a force against the user's ear can provide for reducing deformation of a user's ear due to the usage of earwear. The ear adapter assembly 10 provides for improved comfort for a user wearing earwear, especially when concurrently wearing both earwear and eyewear. In professional applications, particular industries require the concurrent use of earwear for noise protection, or communications, alongside eyewear for eye protection or the ability to see effectively. Utilizing the ear adapter assembly 10 can provide for improved comfort for those working or involved in such industries. Furthermore, the cushions 12 for the ear adapter assembly 10 can be comprised of one or more individual cushions that are easily tailored to a wide range of ear and head shapes of the users.

To the extent not already described, the different features and structures of the various embodiments can be used in combination, or in substitution with each other as desired. That one feature is not illustrated in all of the embodiments is not meant to be construed that it cannot be so illustrated, but is done for brevity of description. Thus, the various features of the different embodiments can be mixed and matched as desired to form new embodiments, whether or not the new embodiments are expressly described. All combinations or permutations of features described herein are covered by this disclosure.

This written description uses examples to describe aspects of the disclosure described herein, including the best mode, and also to enable any person skilled in the art to practice aspects of the disclosure, including making and using any devices or systems and performing any incorporated methods. The patentable scope of aspects of the disclosure is defined by the claims, and can include other examples that occur to those skilled in the art. Such other examples are intended to be within the scope of the claims if they have structural elements that do not differ from the literal languages of the claims, or if they include equivalent structural elements with insubstantial differences from the literal languages of the claims.

What is claimed is:

1. An ear adapter assembly comprising:
a curved channel forming a guide channel;
a cushion positioned at least partially along the curved channel and adapted to fit between a portion of a user's ear and a side of a user's head;
a line extending along the guide channel of the curved channel and through at least a portion of the cushion; cushion; and
a clasp carried by the line wherein the position of the clasp along the line is adapted to alter at least one of the shape of the cushion or the tension of the line, or both.

2. The ear adapter assembly of claim 1 wherein the cushion is made of foam.

3. The ear adapter assembly of claim 1 wherein the cushion has a first side adapted to contact the user's ear and a second side opposite the first side.

4. The ear adapter assembly of claim 3 wherein the first side has a smaller cross-sectional area than a cross-sectional area of second side.

5. The ear adapter assembly of claim 3 wherein the cushion has an arcuate geometry contoured to the shape of the user's ear.

6. The ear adapter assembly of claim 1 wherein the guide channel forms a hollow body.

7. The ear adapter assembly of claim 1 wherein the line forms a loop.

8. The ear adapter assembly of claim 1 further comprising an eyewear loop coupled to the line adapted to secure the eyewear loop to an eyewear.

9. The ear adapter assembly of claim 8 wherein the line draws the eyewear loop into a flared opening at the cushion.

10. The ear adapter assembly of claim 1 further comprising a controller configured to selectively adjust a mode of at least one of the line, an eyewear fastener, or a shape of the cushion.

11. The ear adapter assembly of claim 10 wherein the controller comprises a spring.

12. The ear adapter assembly of claim 1 wherein the cushion includes an aperture extending through the cushion and the curved channel and line extend through the aperture.

13. The ear adapter assembly of claim 1 wherein the cushion resists a force from a user's earwear applied to the user's ear is compressing the user's ear toward the user's head.

14. The ear adapter assembly of claim 13 wherein the force applied to the user's ear is an applied lateral force relative to the user's head.

15. The ear adapter assembly of claim 14 wherein the cushion is adapted to reduce deformation of the user's ear.

16. The ear adapter assembly of claim 13 wherein the user's earwear includes one of headphones, a helmet, a headset, headgear, or earmuffs.

17. The ear adapter assembly of claim 1 wherein the cushion reduces deformation of the user's ear against a temple of an eyewear during concurrent use with a user's earwear.

18. An ear adapter assembly for eyewear comprising:
a cushion having a front end and a bottom end, and adapted to be positioned between a user's ear and a user's head;
a curved channel having a hollow body extending at least partially through the cushion and a portion extending from the front end of the cushion, wherein the front end defines a flared opening;

a line extending through the cushion and the curved channel and extending from the front end of the cushion; and an eyewear loop secured by the line, adapted to connect to a temple of the eyewear;

wherein tensioning of the line secures the eyewear loop to the temple of the eyewear and wherein tensioning of the line draws the eyewear loop into the flared opening.

19. An ear adapter assembly comprising:

a curved channel having a hollow body;

a cushion extending at least partially along the curved channel and adapted to fit between a pinna portion of a user's ear and a side of a user's head;

a line extending axially along the hollow body of the curved channel and through at least a portion of the cushion; and a spring configured to selectively adjust a mode of at least one of the line, an eyewear fastener, or a shape of the cushion.

\* \* \* \* \*

UNITED STATES PATENT AND TRADEMARK OFFICE
CERTIFICATE OF CORRECTION

PATENT NO. : 11,567,343 B2
APPLICATION NO. : 16/713151
DATED : January 31, 2023
INVENTOR(S) : Eugene Manin It is certified that error appears in the above-identified patent and that said Letters Patent is hereby corrected as shown below:

In the Claims

Column 16, Lines 8-10, Claim 1:
"through at least a portion of the cushion;
cushion and;
a clasp ..."

Should be:
"through at least a portion of the cushion;
a clasp ..."

Signed and Sealed this
Sixteenth Day of July, 2024

Katherine Kelly Vidal
*Director of the United States Patent and Trademark Office*